(12) United States Patent  
Heuser

(10) Patent No.: US 7,402,141 B2  
(45) Date of Patent: Jul. 22, 2008

(54) CATHETER GUIDEWIRE SYSTEM USING CONCENTRIC WIRES

(76) Inventor: Richard R. Heuser, 500 W. Thomas Rd., Suite 900, Phoenix, AZ (US) 85013

( * ) Notice: Subject to any disclaimer, the term of this patent is extended or adjusted under 35 U.S.C. 154(b) by 0 days.

(21) Appl. No.: 10/927,340

(22) Filed: Aug. 25, 2004

(65) Prior Publication Data

US 2006/0047222 A1 Mar. 2, 2006

Related U.S. Application Data

(60) Provisional application No. 60/498,427, filed on Aug. 27, 2003.

(51) Int. Cl.
*A61B 5/00* (2006.01)
*A61M 25/00* (2006.01)

(52) U.S. Cl. ..................................... 600/585

(58) Field of Classification Search ................. 600/433, 600/434, 435, 585; 604/164.13
See application file for complete search history.

(56) References Cited

U.S. PATENT DOCUMENTS

| | | |
|---|---|---|
| 2,729,211 A | 1/1956 | Peter |
| 3,751,305 A | 8/1973 | Huebscher |
| 3,788,318 A | 1/1974 | Kim et al. |
| 3,828,770 A | 8/1974 | Kuris et al. |
| 3,828,782 A | 8/1974 | Polin |
| 4,000,739 A | 1/1977 | Stevens |
| 4,241,289 A | 12/1980 | Bowling |
| 4,430,081 A | 2/1984 | Timmermans |

(Continued)

FOREIGN PATENT DOCUMENTS

EP 0696447 2/1996

(Continued)

OTHER PUBLICATIONS

Baffour, M.S.C., R. et al. "An Angiographic Study of Ischemia as a Determinant of Neovascularization in Arteriovenous Reversal." Surgery, Gynecology & Obstetrics. Jan. 1988. pp. 28-32. vol. 166.

(Continued)

*Primary Examiner*—Max F. Hindenburg
*Assistant Examiner*—Jonathan M Foreman
(74) *Attorney, Agent, or Firm*—Kolisch Hartwell, P.C.

(57) ABSTRACT

A catheterization guidewire system provides a first wire for percutaneous insertion in a blood vessel. The first wire may include a lumen running from one end to the other, and a handle adjacent the proximal end for manipulation of the first wire about and along a central axis. A second wire may be inserted in the blood vessel over the first wire, and may have a handle adjacent a proximal end. With the first and second wires coupled together, either of the handles of the first and second wires may be used to manipulate both wires. The wires may be manipulated relative to one another by simultaneous use of both handles. The first wire may have a rigidity selected to allow crossing of a bifurcation in the blood vessel. A third wire, which may also have a handle, may be inserted in the blood vessel over the second wire. A catheter for insertion over at least one of the first, second, and third wires may be provided with a balloon and a stent placement apparatus.

8 Claims, 3 Drawing Sheets

U.S. PATENT DOCUMENTS

| | | |
|---|---|---|
| 4,445,892 A | 5/1984 | Hussein et al. |
| 4,590,669 A | 5/1986 | Imamura |
| 4,634,342 A | 1/1987 | Rodewald |
| 4,634,432 A | 1/1987 | Kocak |
| 4,637,814 A | 1/1987 | Leiboff |
| 4,650,466 A | 3/1987 | Luther |
| 4,650,472 A | 3/1987 | Bates |
| 4,682,981 A | 7/1987 | Suzuki et al. |
| 4,705,511 A | 11/1987 | Kocak |
| 4,706,671 A | 11/1987 | Weinrib |
| 4,744,364 A | 5/1988 | Kensey |
| 4,771,777 A | 9/1988 | Horzewski et al. |
| 4,772,258 A | 9/1988 | Marangoni et al. |
| 4,796,640 A | 1/1989 | Webler |
| 4,832,688 A | 5/1989 | Sagae et al. |
| 4,862,891 A | 9/1989 | Smith |
| 4,874,378 A | 10/1989 | Hillstead |
| 4,883,460 A | 11/1989 | Zanetti |
| 4,895,564 A | 1/1990 | Farrell |
| 4,911,163 A | 3/1990 | Fina |
| 4,950,257 A | 8/1990 | Hibbs et al. |
| 4,994,071 A | 2/1991 | MacGregor |
| 5,078,684 A | 1/1992 | Yasuda |
| 5,092,846 A | 3/1992 | Nishijima et al. |
| 5,112,310 A | 5/1992 | Grobe |
| 5,147,336 A | 9/1992 | Wendell et al. |
| 5,163,906 A | 11/1992 | Ahmadi |
| 5,176,144 A | 1/1993 | Yoshikoshi et al. |
| 5,183,470 A * | 2/1993 | Wettermann ............... 604/523 |
| 5,199,939 A | 4/1993 | Dake et al. |
| 5,207,228 A | 5/1993 | Roelandt et al. |
| 5,213,417 A | 5/1993 | Yamada et al. |
| 5,217,019 A | 6/1993 | Hughes |
| 5,217,484 A | 6/1993 | Marks |
| 5,234,437 A | 8/1993 | Sepetka |
| 5,242,410 A | 9/1993 | Melker |
| 5,256,141 A | 10/1993 | Gencheff et al. |
| 5,256,158 A | 10/1993 | Tolkoff et al. |
| 5,257,979 A | 11/1993 | Jagpal |
| 5,261,878 A | 11/1993 | Galindo |
| 5,267,966 A | 12/1993 | Paul |
| 5,275,488 A | 1/1994 | Stelts |
| 5,281,793 A | 1/1994 | Gavin et al. |
| 5,290,310 A | 3/1994 | Makower et al. |
| 5,292,311 A | 3/1994 | Cope |
| 5,320,617 A | 6/1994 | Leach |
| 5,330,486 A | 7/1994 | Wilk |
| 5,354,271 A | 10/1994 | Voda |
| 5,356,486 A | 10/1994 | Sugarman et al. |
| 5,364,392 A | 11/1994 | Warner et al. |
| 5,370,459 A | 12/1994 | Culbertson et al. |
| 5,380,304 A | 1/1995 | Parker |
| 5,395,341 A | 3/1995 | Slater |
| 5,399,088 A * | 3/1995 | Mechley ...................... 433/20 |
| 5,403,341 A * | 4/1995 | Solar ........................... 606/198 |
| 5,415,635 A | 5/1995 | Bagaoisan et al. |
| 5,423,774 A | 6/1995 | Fischell et al. |
| 5,437,292 A | 8/1995 | Kipshidze et al. |
| 5,439,446 A | 8/1995 | Barry |
| 5,443,478 A | 8/1995 | Purdy |
| 5,445,646 A | 8/1995 | Euteneuer et al. |
| 5,458,573 A | 10/1995 | Summers |
| 5,462,359 A | 10/1995 | Reichl et al. |
| 5,462,529 A | 10/1995 | Simpson et al. |
| 5,466,230 A | 11/1995 | Davila |
| 5,499,975 A | 3/1996 | Cope et al. |
| 5,512,291 A | 4/1996 | Li |
| 5,514,236 A | 5/1996 | Avellanet et al. |
| 5,545,193 A | 8/1996 | Fleischman et al. |
| 5,545,209 A | 8/1996 | Roberts et al. |
| 5,549,626 A | 8/1996 | Miller et al. |
| 5,578,008 A | 11/1996 | Hara |
| 5,591,137 A | 1/1997 | Stevens |
| 5,591,206 A | 1/1997 | Moufarrege |
| 5,599,325 A | 2/1997 | Ju et al. |
| 5,620,457 A | 4/1997 | Pinchasik et al. |
| 5,628,786 A | 5/1997 | Banas et al. |
| 5,632,760 A | 5/1997 | Sheiban et al. |
| 5,632,762 A | 5/1997 | Myler |
| 5,645,560 A | 7/1997 | Crocker et al. |
| 5,660,473 A | 8/1997 | Noma et al. |
| 5,665,107 A | 9/1997 | Hammerslag |
| 5,667,523 A | 9/1997 | Bynon et al. |
| 5,674,241 A | 10/1997 | Bley et al. |
| 5,681,295 A | 10/1997 | Gyure et al. |
| 5,683,453 A | 11/1997 | Palmaz |
| 5,688,266 A | 11/1997 | Edwards et al. |
| 5,695,498 A | 12/1997 | Tower |
| 5,707,359 A | 1/1998 | Bufalini |
| 5,725,524 A | 3/1998 | Mulier et al. |
| 5,725,572 A | 3/1998 | Lam et al. |
| 5,728,068 A | 3/1998 | Leone et al. |
| 5,733,044 A | 3/1998 | Rose et al. |
| 5,733,267 A | 3/1998 | Del Toro |
| 5,735,892 A | 4/1998 | Myers et al. |
| 5,743,900 A | 4/1998 | Hara |
| 5,749,880 A | 5/1998 | Banas et al. |
| 5,762,630 A | 6/1998 | Bley et al. |
| 5,769,077 A | 6/1998 | Lindegren |
| 5,792,070 A | 8/1998 | Kauphusman et al. |
| 5,800,393 A | 9/1998 | Sahota |
| 5,800,520 A | 9/1998 | Fogarty et al. |
| 5,807,350 A | 9/1998 | Diaz |
| 5,814,016 A | 9/1998 | Valley et al. |
| 5,814,064 A | 9/1998 | Daniel et al. |
| 5,820,607 A | 10/1998 | Tcholakian et al. |
| 5,830,222 A | 11/1998 | Makower |
| 5,830,224 A | 11/1998 | Cohn et al. |
| 5,833,644 A | 11/1998 | Zadno-Azizi et al. |
| 5,833,650 A | 11/1998 | Imran |
| 5,843,124 A | 12/1998 | Hammerslag |
| 5,843,166 A | 12/1998 | Lentz et al. |
| 5,853,409 A | 12/1998 | Swanson et al. |
| 5,855,563 A | 1/1999 | Kaplan et al. |
| 5,857,998 A | 1/1999 | Barry |
| 5,868,705 A * | 2/1999 | Bagaoisan et al. ..... 604/103.11 |
| 5,868,708 A | 2/1999 | Hart et al. |
| 5,893,867 A | 4/1999 | Bagaoisan et al. |
| 5,897,497 A | 4/1999 | Fernandez |
| 5,899,917 A | 5/1999 | Edwards et al. |
| 5,906,636 A | 5/1999 | Casscells, III et al. |
| 5,911,710 A | 6/1999 | Barry et al. |
| 5,916,264 A | 6/1999 | Von Oepen |
| 5,928,260 A | 7/1999 | Chin et al. |
| 5,928,279 A | 7/1999 | Shannon et al. |
| 5,935,075 A | 8/1999 | Casscells et al. |
| 5,938,694 A | 8/1999 | Jaraczewski et al. |
| 5,944,019 A | 8/1999 | Knudson et al. |
| 5,957,961 A | 9/1999 | Maguire et al. |
| 5,964,798 A | 10/1999 | Imran |
| 5,968,064 A | 10/1999 | Selmon et al. |
| 5,976,178 A | 11/1999 | Goldsteen et al. |
| 5,980,532 A | 11/1999 | Wang |
| 5,984,955 A | 11/1999 | Wisselink |
| 5,989,223 A | 11/1999 | Chu et al. |
| 5,997,526 A | 12/1999 | Giba et al. |
| 6,004,310 A | 12/1999 | Bardsley et al. |
| 6,013,085 A | 1/2000 | Howard |
| 6,017,365 A | 1/2000 | Von Oepen |
| 6,019,779 A | 2/2000 | Thorud et al. |

| | | | |
|---|---|---|---|
| 6,022,336 A | 2/2000 | Zadno-Azizi et al. | |
| 6,022,343 A | 2/2000 | Johnson et al. | |
| 6,030,406 A | 2/2000 | Davis et al. | |
| 6,033,434 A | 3/2000 | Borghi | |
| 6,064,902 A | 5/2000 | Haissaguerre et al. | |
| 6,068,656 A | 5/2000 | Von Oepen | |
| 6,071,292 A | 6/2000 | Makower et al. | |
| 6,120,534 A | 9/2000 | Ruiz | |
| 6,124,523 A | 9/2000 | Banas et al. | |
| 6,156,064 A | 12/2000 | Chouinard | |
| 6,159,197 A | 12/2000 | Heuser | |
| 6,168,579 B1 | 1/2001 | Tsugita | |
| 6,176,872 B1 | 1/2001 | Miksza | |
| 6,187,033 B1 | 2/2001 | Schmitt et al. | |
| 6,190,353 B1 | 2/2001 | Makower et al. | |
| 6,193,747 B1 | 2/2001 | Von Oepen | |
| 6,231,587 B1 | 5/2001 | Makower | |
| 6,245,052 B1 | 6/2001 | Orth et al. | |
| 6,264,685 B1 | 7/2001 | Ahari | |
| 6,264,690 B1 | 7/2001 | Von Oepen | |
| 6,283,958 B1 | 9/2001 | Vogl et al. | |
| 6,308,090 B1 * | 10/2001 | Tu et al. | 600/374 |
| 6,325,826 B1 | 12/2001 | Vardi et al. | |
| 6,364,900 B1 | 4/2002 | Heuser | |
| 6,383,214 B1 | 5/2002 | Banas et al. | |
| 6,408,214 B1 * | 6/2002 | Williams et al. | 607/122 |
| 6,464,665 B1 | 10/2002 | Heuser | |
| 6,464,684 B1 | 10/2002 | Galdonik | |
| 6,475,226 B1 | 11/2002 | Belef et al. | |
| 6,530,914 B1 * | 3/2003 | Mickley | 604/528 |
| 6,536,949 B1 | 3/2003 | Heuser | |
| 6,582,394 B1 | 6/2003 | Reiss et al. | |
| 6,613,078 B1 | 9/2003 | Barone | |
| 6,638,268 B2 * | 10/2003 | Niazi | 604/528 |
| 6,709,455 B1 | 3/2004 | Chouinard | |
| 6,726,677 B1 | 4/2004 | Flaherty et al. | |
| 6,746,479 B2 | 6/2004 | Ehr et al. | |
| 6,830,568 B1 * | 12/2004 | Kesten et al. | 606/15 |
| 6,858,038 B2 | 2/2005 | Heuser | |
| 6,863,684 B2 | 3/2005 | Kim et al. | |
| 6,866,805 B2 | 3/2005 | Hong et al. | |
| 6,929,009 B2 | 8/2005 | Makower et al. | |
| 6,987,660 B2 | 1/2006 | Stevenson et al. | |
| 7,056,325 B1 | 6/2006 | Makower et al. | |
| 7,059,330 B1 | 6/2006 | Makower et al. | |
| 7,094,230 B2 | 8/2006 | Flaherty et al. | |
| 7,134,438 B2 | 11/2006 | Makower et al. | |
| 7,159,592 B1 | 1/2007 | Makower et al. | |
| 7,166,088 B2 | 1/2007 | Heuser | |
| 7,179,250 B2 | 2/2007 | Heuser | |
| 7,179,270 B2 | 2/2007 | Makower | |
| 7,191,015 B2 | 3/2007 | Lamson et al. | |
| 2001/0003161 A1 | 6/2001 | Vardi et al. | |
| 2001/0049549 A1 | 12/2001 | Boylan et al. | |
| 2002/0178570 A1 | 12/2002 | Sogard et al. | |
| 2003/0055402 A1 * | 3/2003 | Zhou | 604/531 |
| 2003/0055484 A1 | 3/2003 | Lau et al. | |
| 2003/0130598 A1 * | 7/2003 | Manning et al. | 600/585 |
| 2003/0139797 A1 | 7/2003 | Johnson et al. | |
| 2003/0163156 A1 | 8/2003 | Hebert et al. | |
| 2003/0199967 A1 | 10/2003 | Hartley et al. | |
| 2003/0212450 A1 | 11/2003 | Schlick | |
| 2004/0019373 A1 | 1/2004 | Casey et al. | |
| 2004/0082989 A1 | 4/2004 | Cook et al. | |
| 2004/0098095 A1 | 5/2004 | Burnside et al. | |
| 2004/0106978 A1 | 6/2004 | Greenberg et al. | |
| 2004/0116831 A1 | 6/2004 | Vrba | |
| 2004/0162603 A1 | 8/2004 | Golds et al. | |
| 2004/0167607 A1 | 8/2004 | Frantzen | |
| 2005/0125011 A1 | 6/2005 | Spence et al. | |
| 2006/0047222 A1 | 3/2006 | Heuser | |
| 2006/0217799 A1 | 9/2006 | Mailander et al. | |
| 2006/0229638 A1 | 10/2006 | Abrams et al. | |
| 2007/0021730 A1 | 1/2007 | Flaherty et al. | |
| 2007/0083257 A1 | 4/2007 | Pal et al. | |

FOREIGN PATENT DOCUMENTS

| | | |
|---|---|---|
| EP | 0707864 | 4/1996 |
| EP | 0819411 | 1/1998 |
| EP | 0917886 | 5/1999 |
| EP | 1421970 | 5/2004 |
| FR | 2753907 | 3/1998 |
| JP | 0003094773 | 4/1991 |
| WO | WO9214406 | 9/1992 |
| WO | WO9640348 | 12/1996 |
| WO | WO9717101 | 5/1997 |
| WO | WO9800090 | 1/1998 |
| WO | WO9811933 | 3/1998 |
| WO | WO9819632 | 5/1998 |
| WO | WO9826731 | 6/1998 |
| WO | WO9839047 | 9/1998 |
| WO | WO9908744 | 2/1999 |
| WO | WO9913808 | 3/1999 |
| WO | WO9924105 | 5/1999 |
| WO | WO9934749 | 7/1999 |
| WO | WO9936002 | 7/1999 |
| WO | WO0166038 | 3/2001 |
| WO | WO0596995 | 10/2005 |

OTHER PUBLICATIONS

Blaisdell, M.D., William, et al. "Revascularization of Severely Ischemic Extremeties with an Arteriovenous Fistula." American Journal of Surgery. Aug. 1966. pp. 166-174. vol. 112.

Cuttino Jr., John, et al. "Collateral Vessel Formation: Isolation of a Transferrable Factor Promoting a Vascular Response." Basic Research in Cardiology. Jan. 9, 1975. pp. 568-573. vol. 70, No. 5.

Elsner, M.D., Mathias, et al. "Coronary Stent Grafts Covered by a Polytetrafluoroethylene Membrane." The American Journal of Cardiology. Aug. 1, 1999. pp. 335-338. vol. 84.

English Abstract of JP0003094773 of Inaba et al.

Gerard, M.D., Dava, et al. "Acute Physiologic Effects of Arteriovenous Anastomosis and Fistula in Revascularizing the Ischemic Canine Hind Limb." Surgery. Apr. 1981. pp. 485-493. vol. 89, No. 4.

Goldsmith, M.D., Harry, et al. "Lipid Angiogenic Factor from Omentum." JAMA. Oct. 19, 1984. pp. 2034-2036. vol. 252, No. 15.

Halstead, M.D., Albert. "Arteriovenous Anastomosis in the Treatment of Gangrene in the Extremities." Surgery, Gynecology and Obstetrics. 1912. pp. 1-19. vol. 16.

Heuser, M.D., Richard R., et al. "Endoluminal Grafting for Percutaneous Aneurysm Exclusion in an Aortocoronary Saphenous Vein Graft: The First Clinical Experience." Journal of Endovascular Surgery. 1995. pp. 81-88. vol. 2.

Howell, M.D., Marcus, et al. "Preliminary Results of Endovascular Abdominal Aortic Aneurysm Exclusion with the AneuRx Stent-Graft." Journal of the American College of Cardiology. 2001. pp. 1040-1048. vol. 38, No. 4.

Johnson & Johnson Gateway, LLC. "Chronic Total Occlusion (CTO) Technologies." http://www.jnjgateway.com/home.jhtml?loc=USENG&page=viewContent&contentId=09008b9881163810&parentId=09008b9881163810. 2007. Printed Jan. 17, 2007.

Kalmar, M.D., Gabor, et al. "Radial Force and Wall Apposition of Balloon-expandable Vascular Stents in Eccentric Stenoses: An In Vitro Evaluation in a Curved Vessel Model." Journal of Vascular and Interventional Radiology. May 2002. pp. 499-508. vol. 13, No. 5.

Kumar, S. et al. "Angiogenesis Factor from Human Myocardial Infarcts." The Lancet. Aug. 13, 1983. pp. 364-368.

Matolo, M.D., Nathaniel. "Use of an Arteriovenous Fistula for Treatement of the Severely Iscemic Extremity: Experimental Evaluation." Ann. Surg. Nov. 1976. pp. 622-625. vol. 184, No. 5.

Oesterle, et al. "An Embolization Containment Device." Catheterization and Cardiovascular Interventions. 1999. pp. 243-250. vol. 47.

Robertson, M.D., Roy, et al. "Collateral Circulation in the Presence of Experimental Arteriovenous Fistula." Surgery. Jan. 1950. pp. 1-16. vol. 27, No. 1.

Root, M.D., Harlan, et al. "Effects of an Arteriovenous Fistula on the Devascularized Limb." JAMA. Feb. 22, 1965. pp. 109-112. vol. 191, No. 8.

Rossi, Anne V. "510(k) Summary per 21 CFR 807.92 re BSC IQ Hydrophilic Guide Wire and Response Letter from Department of Health and Human Services." Aug. 1, 2003.

Sheil, A.G.R. "Treatment of Critical Ischaemia of the Lower Limb by Venous Arterialization: an Interim Report." Br. J. Surg. 1977. pp. 197-199.

Terumo Medical Corporation. "Glidewire Hydrophilic Coated Guidewire Designed for Peripheral Applications." http://www.terumomedical.com/SubDepts.asp?myID=79. 2002. Printed Jan. 30, 2007.

* cited by examiner

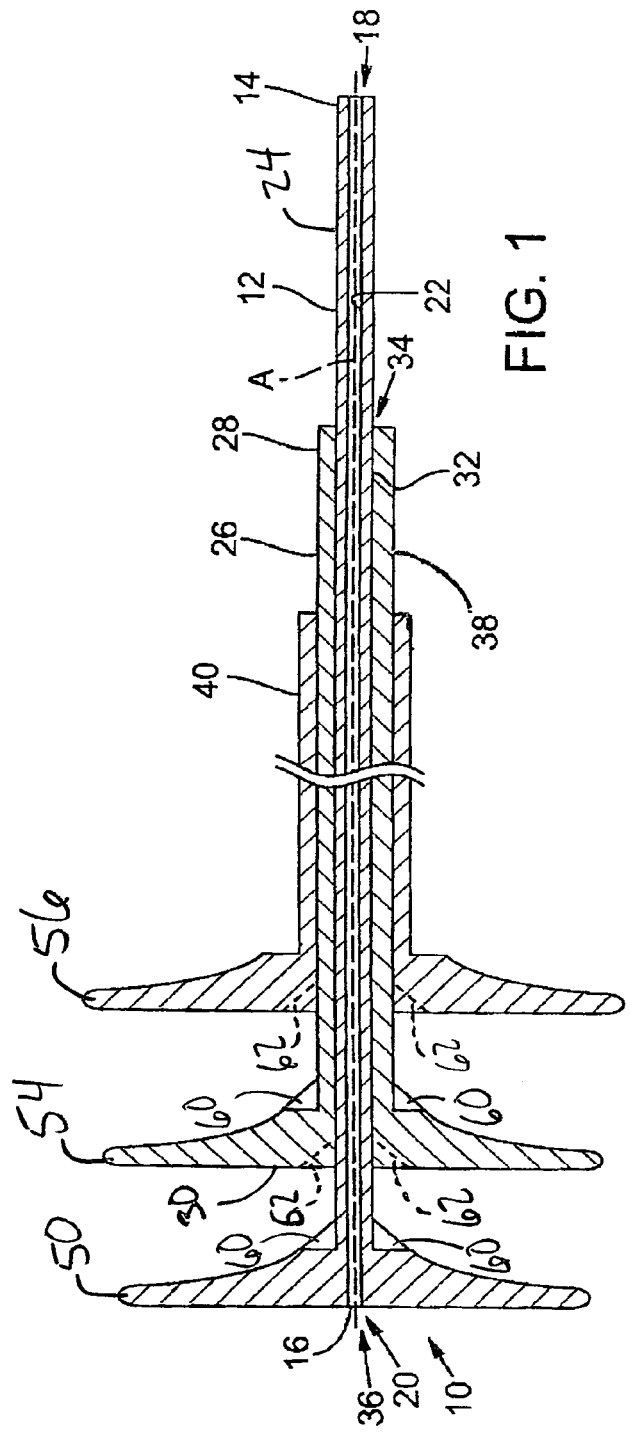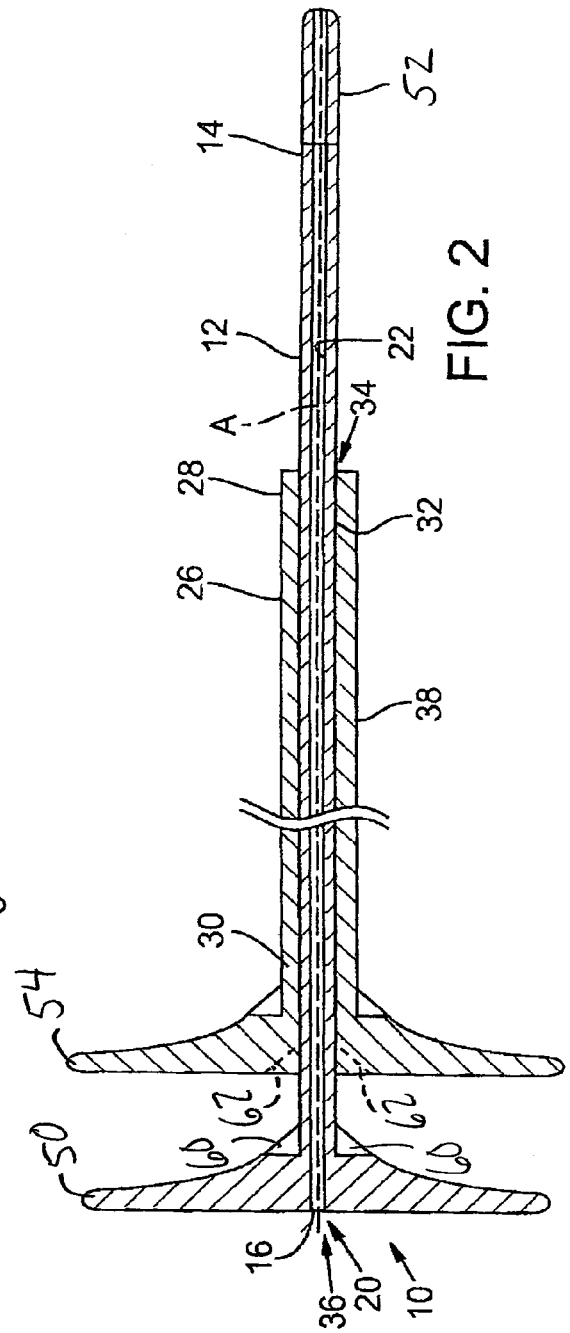

CATHETER GUIDEWIRE SYSTEM USING CONCENTRIC WIRES

RELATED APPLICATION

This application is based upon and claims priority under 35 U.S.C. § 119(e) to U.S. Provisional Patent Application Ser. No. 60/498,427, entitled "CATHETER GUIDEWIRE SYSTEM USING CONCENTRIC WIRES," and filed on Aug. 27, 2003.

BACKGROUND

The present invention relates to a guidewire system for insertion into human blood vessels for treatment and diagnostic procedures, and more particularly relates to multiple concentric wires in the guidewire system for maneuvering through bends, bifurcations, narrowing vessels, and other complications within the human blood vessels.

SUMMARY

The invented guidewire system provides for inserting and maneuvering a guidewire for deployment of a treatment device within a human blood vessel. Typically, guidewires are inserted percutaneously into a relatively large artery or vein in one of the patient's legs. Depending on the location of the area to be investigated or treated within the patient, the wire may then be maneuvered upwards toward the heart, or contralaterally across the iliac bifurcation to gain access to the patient's other leg. The iliac bifurcation is one example of many bends and intersections within the human blood vessel system that present difficulties in maneuvering the forward tip of the wire to allow the wire to reach the desired location.

The present invention provides two, three, or more hollow, concentric wires, coupled together for insertion into the human blood vessel with each wire having one or more attributes selected for use in maneuvering across the bends and intersections between the site of insertion and the location for investigation and treatment. For example, each of the wires may be made hydrophilic to an extent selected among various degrees, and/or made stiff to a selected degree, provided with hydrophilic and stiff sections, and be transitionless or have transitions between the hydrophilic and stiff sections. The multiple wires may have independently selected attributes different from one another so that each may be beneficially used in maneuvering across the different types of bends and intersections and along blood vessels of varying sizes to reach the treatment or diagnostic site. A treatment or diagnostic device may be provided on one or more of the wires, typically adjacent the distal tip, including devices providing laser or radiofrequency energy, or optical coherent reflectometry (OCR).

BRIEF DESCRIPTION OF THE DRAWINGS

FIG. 1 is a cross-sectional side view of a guidewire system according to an embodiment of the present invention showing three concentric wires, including their proximal and distal ends, central lumens, and proximal handles.

FIG. 2 is a cross-sectional side view of a guidewire system according to an embodiment of the present invention showing two concentric wires, and showing a treatment/diagnostic device at the distal tip of the inner wire.

DETAILED DESCRIPTION OF THE PREFERRED EMBODIMENTS

Figure 3A:
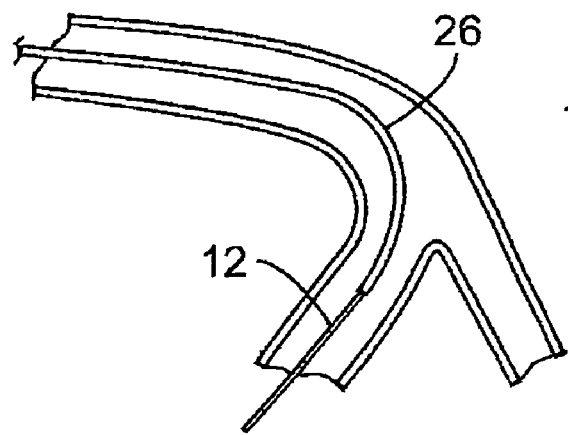
FIGS. 3A and 3B are a cross sectional view of two guidewires extending around a bend adjacent a bifurcation in a human blood vessel, showing the difference in performance between a transitionless wire (3A) and a wire with a transition (3B).

As shown in FIGS. 1 and 2, an embodiment of the guidewire system of the present invention is a multiple wire system, indicated generally at 10. System 10 may include an inner wire 12 having a distal end 14 and a proximal end 16. Inner wire 12 has a length that may be selected for a particular type of procedure to be conducted in a human blood vessel, e.g., between about 180-cm and about 300-cm. Inner wire 12 may include an opening 18 adjacent distal end 14 and an opening 20 adjacent proximal end 16, and a central lumen 22 extending between the proximal and distal openings. Central lumen 22 defines an inner diameter for wire 12, and wire 12 also has a generally cylindrical outer surface 24 defining an outer diameter. Typically, the outer diameter of inner wire 12 is between about 0.004 and 0.014 inches, and may be any size therebetween, or larger or smaller as selected for the desired procedure and for compatibility with other wires, catheters, sheaths, and other equipment.

Inner wire 12 is preferably provided with a handle 50, preferably removable, adjacent proximal end 16 that the physician may use in manipulating the wire about and along a central axis A of the wire. Preferably wire 12 is constructed with a hydrophilic material selected for the particular procedure. For example, coating with Teflon or plastic covering makes a wire hydrophilic.

Wire 12 is preferably constructed without transitions between sections, if it includes any sections, of the wire. Inner wire 12 may be used in crossing a bifurcation in the human blood vessel, and may be provided with a rigidity selected to allow the bifurcation crossing. Rigidity is typically controlled by the use of braiding or the selection of various materials. For example, nitinol is flexible, but it becomes stiffer as more stainless steel is added.

As best seen in FIG. 2, inner wire 12 may optionally include a treatment or a diagnostic device 52, typically located at the distal end 14 of wire 12. Alternatively, device 52 may be located in a more proximal position on wire 12, or may be located on the other wires or catheter to be described below. Device 52 may be any type of device useful for treating or diagnosing conditions in blood vessels, such as a radiofrequency energy device, a laser energy device, an optical coherent reflectometry (OCR) device, an ultrasound device, or any other device suitable for mounting on a wire or catheter and for controlling from outside the body while inserted in the body.

A second wire 26, preferably constructed to be deployed over inner wire 12, includes a distal end 28 and a proximal end 30 and a length preferably selected to be compatible with inner wire 12. A central lumen 32 of wire 26 extends between a distal opening 34 and a proximal opening 36.

Central lumen 32 of second wire 26 defines an inner diameter for the wire. Wire 26 typically has a generally cylindrical outer surface 38 defining an outer diameter. Typically the outer diameter of wire 26 is between about 0.008 and 0.035 inches, and may be any size therebetween, or larger or smaller as selected for the desired procedure and for compatibility with other wires, catheters, sheaths, and other equipment.

Wire 26 is preferably provided with a handle 54, preferably removable, adjacent proximal end 30 that the physician may use in manipulating the wire about and along a central axis A of the wire. Preferably, second wire 26 has a rigidity selected to be greater than that of inner wire 12, thus providing the system with an overall variable rigidity which depends on the extent to which the inner wire extends out of the second wire.

System 10 may also include a third or outer wire 40, as shown in FIG. 1, preferably having proximal and distal ends with openings and a central lumen communicating therebetween, inner and outer diameters, and a generally cylindrical outer surface as for the other wires. Preferably third wire 40 is sized to fit over the second wire and includes a handle 56, preferably removable, coupled adjacent the proximal end for manipulation of the third wire about and along central axis A. Preferably, third wire 40 has a rigidity selected to be greater than the rigidity of the first wire and greater than the rigidity of the second wire, thus providing the system with an overall variable rigidity which depends on the extent to which the inner wire extends out of the second wire, and the extent to which the second wire extends out of the third wire.

Third wire 40 preferably has an outer diameter between about 0.010-inches and about 0.035-inches, and may be any size therebetween, or larger or smaller as selected for the desired procedure and for compatibility with other wires, catheters, sheaths, and other equipment. Typically, the length of the third wire is less than the length of the second wire, and the length of the second wire is less than that of the inner wire.

Figure 6:
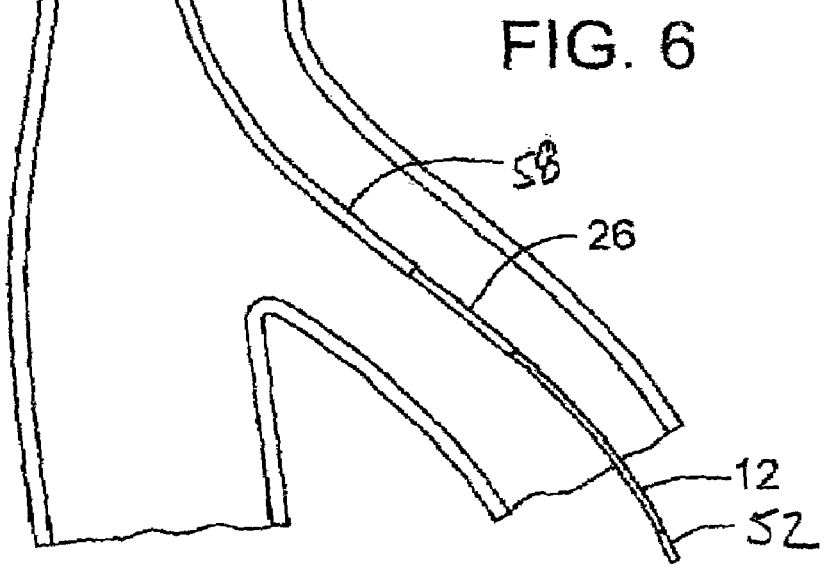
FIG. 6 is a cross sectional view of a two-wire guidewire system with catheter being maneuvered into a branch of a blood vessel.

The multiple guidewire system may be combined with a catheter, such as catheter 58 as shown in FIG. 6, that can be inserted over the wires. Such a catheter may include a balloon and a stent placement apparatus. As described above, the catheter or one or more of the wires may be provided with a radio-frequency energy device, a laser energy device, and/or an optical reflectometry device for applying treatment within the blood vessel, or with other devices, including diagnostic devices such as ultrasound.

Preferably, when the first, second, and third wires are coupled together, any of the handles of the first, second, and third wires may be used to manipulate all three wires, and also the wires may be manipulated relative to one another by simultaneous use of two or three of the handles. For example, as shown in FIGS. 1 and 2, handles 50 and 54 may include one or more forward-facing wings 60, which interlock with corresponding notches 62 in handles 54 and 56, when the handles are pushed together. When the wings and notches interlock, rotational movement of one handle will also rotate the wire attached to the interlocked handle. Alternatively, any other type of selective interlocking may be used, or the friction between the wires may provide for simultaneous movement, unless the handles are separately manipulated.

Preferably, the length of the first wire is between about 180-cm and about 300-cm, but may be other sizes as desired for particular procedures. Typically, the length of the second wire is about 5-cm less than the first wire, and the length of the third wire is about 5-cm less than the second wire.

Figure 3B:
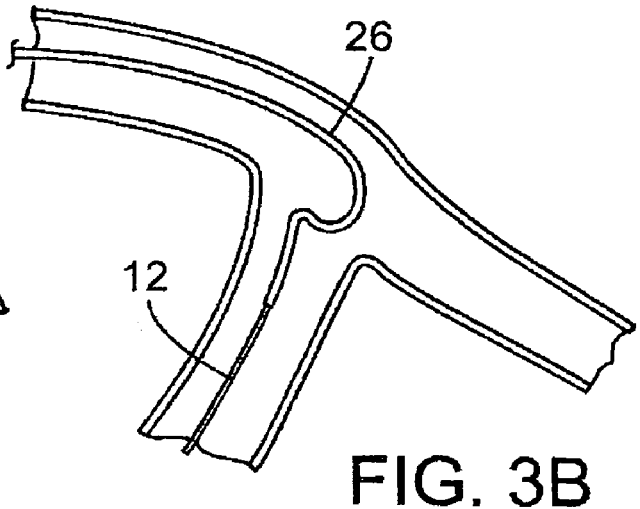

FIGS. 3A and 3B shows two examples of a two-guidewire system, including inner wire 12 and outer wire 26, being used to extend around a bend and into one channel at a bifurcation in a human blood vessel. FIG. 3A shows the performance of a transitionless wire, which can extend around the corner without doubling over, while FIG. 3B shows the performance of a wire with a transition, which tends to double over. The transition typically occurs where two materials that are different in hydrophilicity or stiffness are directly joined, and a transitionless wire is typically provided by gradually changing the hydrophilicity or stiffness, or by other methods of preventing the abrupt transition.

Figure 4:
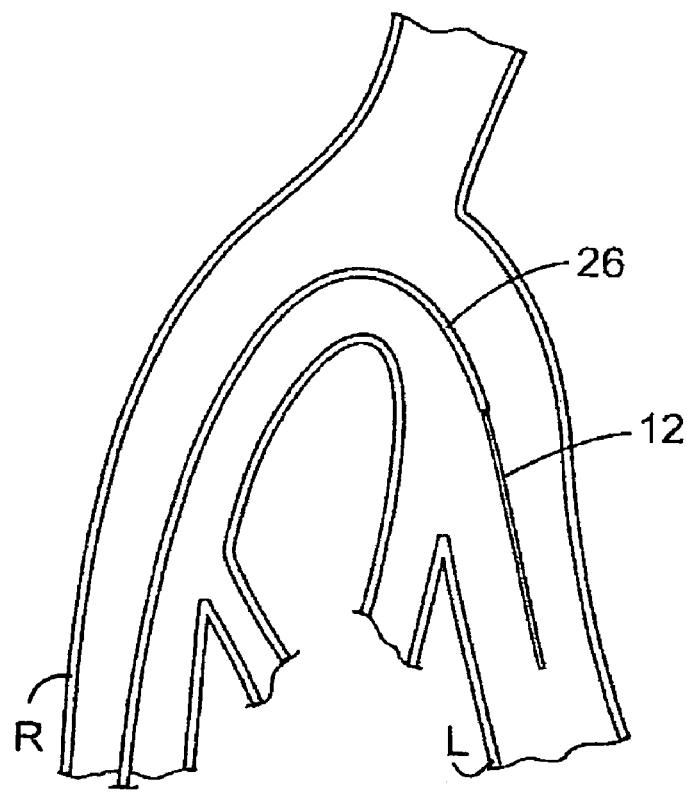
FIG. 4 is a cross sectional view, from a perspective of facing the patient, of contralateral access by the guidewire from the right iliac artery to the left iliac artery.
Figure 5:
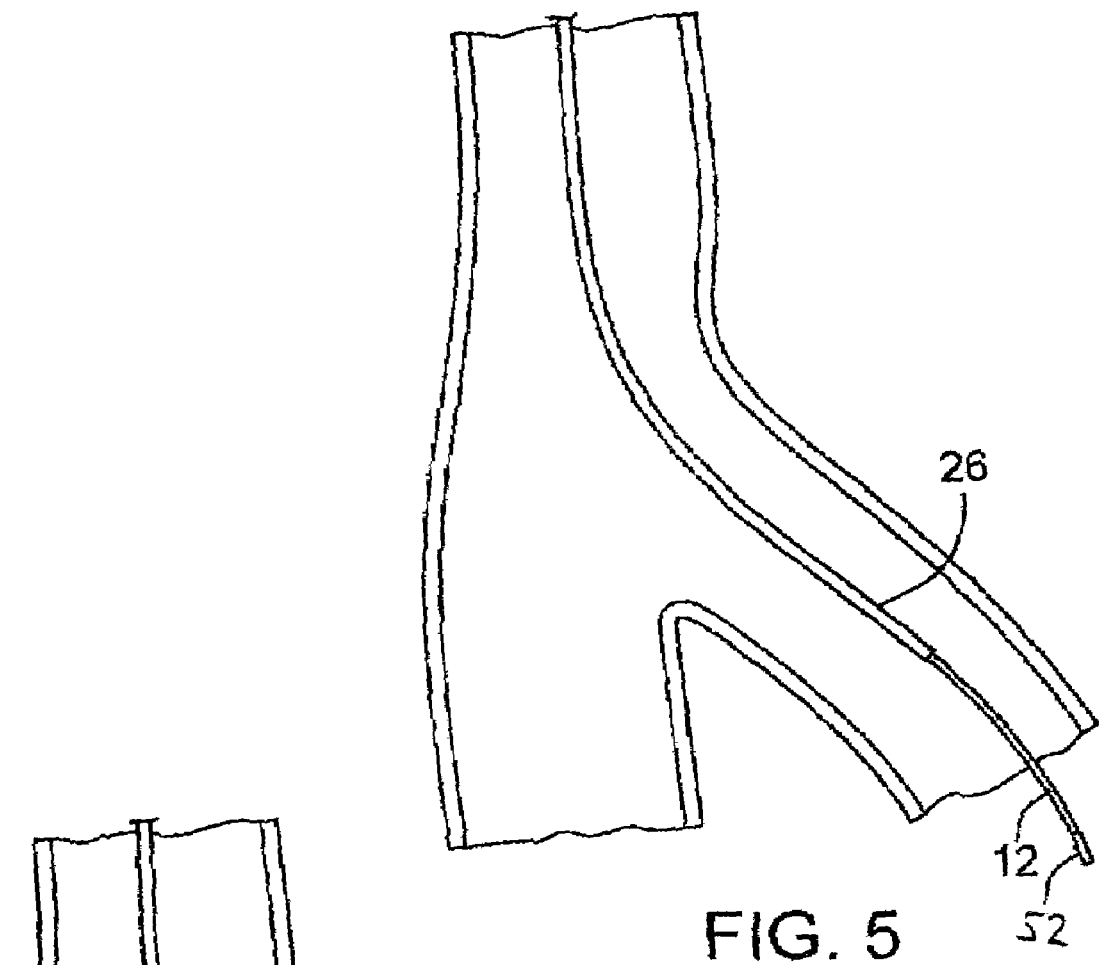
FIG. 5 is a cross sectional view of a two-wire guidewire system being maneuvered into a branch of a blood vessel.

FIG. 4 shows contralateral access by the guidewire system from the right iliac artery R to the left iliac artery L. FIG. 5 shows a two-wire guidewire system, including inner wire 12 and outer wire 26, and treatment/diagnostic device 52, being maneuvered into a branch of a blood vessel. FIG. 6 shows the two-wire guidewire system with catheter 58 being maneuvered into a branch of a blood vessel.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the following claims, and any subsequently presented claims in this or a related application, recite "a" or "a first" element or the equivalent thereof, such claims should be understood to include incorporation of one or more such elements, neither requiring nor excluding two or more such elements.

The claims particularly point out certain combinations and subcombinations that are directed to one of the disclosed inventions and are novel and non-obvious. Inventions embodied in other combinations and subcombinations of features, functions, elements and/or properties may be claimed through amendment of such claims or presentation of new claims in a related application. Such amended or new claims, whether they are directed to a different invention or directed to the same invention, whether different, broader, narrower or equal in scope to the original claims, are also included within the subject matter of the inventions of the present disclosure.

I claim:

1. A guidewire system for use in a catheterization procedure in a human blood vessel, the system including:

a first wire, formed substantially of metal, the first wire configured for percutaneous insertion in the blood vessel, the first wire having a proximal end and a distal end and defining a length dimension therebetween, and wherein the first wire includes an opening adjacent the proximal end and an opening adjacent the distal end, and a central lumen communicating therebetween, the central lumen defining an inner diameter, the first wire having a generally cylindrical outer surface defining an outer diameter, the first wire defining a central longitudinal axis along its length, the first wire further having a handle coupled adjacent the proximal end for manipulation of the first wire about and along the central axis;

a second wire, formed substantially of metal, the second wire configured for percutaneous insertion in the blood vessel over the first wire, the second wire having a proximal end and a distal end and defining a length dimension therebetween, and wherein the second wire includes an opening adjacent the proximal end and an opening adjacent the distal end, and a central lumen communicating therebetween, the central lumen defining an inner diameter, the second wire having a generally cylindrical outer surface defining an outer diameter, the second wire defining a central longitudinal axis along its length, the second wire further having a handle coupled adjacent the proximal end for manipulation of the second wire about and along the central axis, a third wire, formed substantially of metal, the third wire configured for percutaneous insertion in the blood vessel over the second wire, the third wire having a proximal end and a distal end and defining a length dimension therebetween, and wherein the third wire includes an opening adjacent the proximal end and an opening adjacent the distal end, and a central lumen communicating therebetween, the central lumen defining an inner diameter, the third wire having a generally cylindrical outer surface defining an outer diameter, the third wire further having a handle coupled adjacent the proximal end for manipulation of the third wire about and along the central axis, and wherein, with the first, second, and third wires coupled together, any of the handles of the first, second, and third wires may be used to manipulate all three wires, and also wherein the wires may be manipulated relative to one another by simultaneous use of two or three of the handles, and further wherein the first wire is formed substantially of a nitinol alloy, the second wire is formed substantially of a nitinol alloy, and the third wire is formed substantially of a nitinol alloy, and further wherein the compositions of the alloys are varied to produce the greater rigidity of the third wire with respect to the second wire and the greater rigidity of the second wire with respect to the first wire.

2. The guidewire system of claim 1 further wherein the second wire contains a greater proportion of stainless steel as compared to the first wire.

3. The guidewire system of claim 1 wherein one of the first wire, the second wire, and the third wire include a radiofrequency energy device for applying treatment within the blood vessel.

4. The guidewire system of claim 1 where the first wire includes a radiofrequency energy device for applying treatment within the blood vessel.

5. The guidewire system of claim 1 where the second wire includes a radiofrequency energy device for applying treatment within the blood vessel.

6. The guidewire system of claim 1 where the third wire includes a radiofrequency energy device for applying treatment within the blood vessel.

7. The guidewire system of claim 1 wherein the length of the first wire is between about 180-cm and about 300-cm.

8. The guidewire system of claim 7 wherein the length of the second wire is about 5-cm less than the first wire.

* * * * *